United States Patent
D'Halluin

(10) Patent No.: US 6,372,963 B1
(45) Date of Patent: *Apr. 16, 2002

(54) TRANSFORMATION METHOD FOR PLANTS

(75) Inventor: Kathleen D'Halluin, Mariakerke (BE)

(73) Assignee: Aventis CropScience N.V. (BE)

( * ) Notice: Subject to any disclaimer, the term of this patent is extended or adjusted under 35 U.S.C. 154(b) by 0 days.

This patent is subject to a terminal disclaimer.

(21) Appl. No.: 09/480,142

(22) Filed: Jan. 10, 2000

Related U.S. Application Data

(62) Division of application No. 09/026,673, filed on Feb. 20, 1998.
(60) Provisional application No. 60/135,507, filed on Feb. 20, 1998.

(51) Int. Cl.$^7$ .............................. C12N 5/04; C12N 5/10; C12N 15/84; A01H 1/00

(52) U.S. Cl. ..................... 800/294; 435/419; 435/420; 435/469; 800/298

(58) Field of Search ........................... 435/469; 800/294

(56) References Cited

U.S. PATENT DOCUMENTS

| | | |
|---|---|---|
| 5,164,310 A | 11/1992 | Smith et al. |
| 5,177,010 A | 1/1993 | Goldman et al. |
| 5,187,073 A | 2/1993 | Goldman et al. |
| 5,591,616 A | 1/1997 | Hiei et al. |
| 6,140,553 A * | 10/2000 | D'Halluin .................. 800/278 |

FOREIGN PATENT DOCUMENTS

| | | |
|---|---|---|
| EP | 604662 | 7/1994 |
| EP | 672752 | 9/1995 |
| WO | WO89/12102 | 12/1984 |
| WO | 92/09696 | 6/1992 |

OTHER PUBLICATIONS

Rashkova et al, "Characterizaton of Membrane and Protein Interaction Determinants of the *Agrobacterium tumefaciens* VirB11 ATPase", *Journal of Bacteriology* (Feb. 1997) pp. 583–591.

Stephens et al, "*Agrobacterium tumefaciens* VirB11 Protein Requires a Consensus Nucleotide–Binding Site for Function in Virulence", *Journal of Bacteriology* (Jan. 1995) pp. 27–36.

Ward, Jr. et al, "Activity of the Agrobacterium T–DNA Transfer Machinery is Affected by virB Gene Products", *Proc. Nat'l. Acad. Sci. USA*, vol. 88, (Oct. 1991) pp. 9350–9354.

S. Sheikholeslam et al., "Acetosyringone Promotes High Efficiency Transformation of *Arabidopsis thaliana* Explants by *Agrobacterium tumefaciens*", *Plant Molecular Biology* 8:291–298 (1987).

W. Schafer et al., "T–DNA Integration and Expression in a Monocot Crop Plant After Induction of Agrobacterium", *Nature*, 327:529–533 (1987).

D. Raineri et al., "Agrobacterium–Mediated Transformation of Rice (Oryza Sativa L.) ", *Biotechnology* 8:33–38 (1990).

Wen–Hui Shen et al., "T–DNA Transfer to Maize Cells: Histochemical Investigation of β–Glucuronidase Activity in Maize Tissues", *Proc. Natl. Acad. Sci. USA*, 90:148–1492 (1993).

Y. Ishida, et al., "High Efficiency Transformation of Maize (Zea mays L.) Mediated by *Agrobacterium tumefaciens*", *Nature Biotechnology*, vol. 14, Jun. 14, 1996, pp. 745–749.

D. James, et al., "Actosyringone and Osmoprotectants Like Betaine or Proline Synergistically Enhance Agrobacterium–Mediated Transformation of Apple", *Plant Cell Reports*, vol. 12, 1993, pp. 559–563.

B. Jacq, et al., "Factors Influencing T–DNA Transfer in Agrobacterium–Mediated Transformation of Sugarbeet", *Plant Cell Reports*, vol. 12, 1993, pp. 621–624.

S. Satchel, et al., "Identification of the Signal Molecules Produced by Wounded Plant Cells that Activate T–DNA Transfer in *Agrobacterium tumefaciens*", *Nature*, vol. 318, No. 19, Dec. 26, 1985, pp. 624–629.

A. Guivarc'h, et al., "Localization of Target Cells and Improvement of Agrobacterium–Mediated Transformation Efficiency by Direct Acetosyringone Pretreatment of Carrot Root Discs", *Protoplasma*, vol. 174, 1993, pp. 10–18.

M. Chan, et al., "Agrobacterium–Mediated Production of Transgenic Rice Plants Expressing a Chimeric α–Amylase Promoter/β–Glucuronidase Gene", *Plant Molecular Biology*, vol., 22, 1993, pp. 491–506.

B. Bytebier, et al., "T–DNA Organization in Tumor Cultures and Transgenic Plants of the Monocotyledon *Asparagus officinalis*", *Proc. Natl. Acad. Sci.*, vol. 84, Aug. 1987, pp. 5345–5349.

G. Bolton, et al., "Plant Phenolic Compounds Induce Expression of the *Agrobacterium tumefaciens* Loci Needed for Virulence", Science, vol. 232, May 1986, pp. 983–985.

* cited by examiner

*Primary Examiner*—Elizabeth F. McElwain
*Assistant Examiner*—Cynthia Collins
(74) *Attorney, Agent, or Firm*—Burns, Doane, Swecker & Mathis, LLP

(57) ABSTRACT

A process for integrating a DNA fragment into the genome of a cell of a monocotyledonous plant, the process comprising the steps of:

1) incubating, prior to contacting with the DNA fragment, a culture of untransformed monocotyledonous plant cells on a medium comprising a plant phenolic compound, for a period of time sufficient to stimulate cell division and enhance competence for integration of foreign DNA; and 2) contacting the untransformed cells with the DNA fragment under conditions in which the DNA fragment is taken up by the untransformed cells and is stably integrated in the genome of the untransformed cells, to generate transformed cells.

10 Claims, No Drawings

```
                        SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
         (A) LENGTH: 2345 base pairs
         (B) TYPE: nucleic acid
         (C) STRANDEDNESS: double
         (D) TOPOLOGY: linear (ii) MOLECULE TYPE: other nucleic acid
         (A) DESCRIPTION: /desc = "T-DNA of pGSV71"

(ix) FEATURE:
         (A) NAME/KEY: -
         (B) LOCATION: 1..25
         (D) OTHER INFORMATION: /label= RB
             /note= "T-DNA right border"
```

(ix) FEATURE:
    (A) NAME/KEY: -
    (B) LOCATION: 53..1436
    (D) OTHER INFORMATION: /note= "CaMV35S P3 promoter"

(ix) FEATURE:
    (A) NAME/KEY: CDS
    (B) LOCATION: 1437..1988
    (D) OTHER INFORMATION: /product= "phosphinotricin
        actyltransf erase"
        /label= bar
        /note= "region coding for phosphino acetyltransferase"

(ix) FEATURE:
    (A) NAME/KEY: -
    (B) LOCATION: 2007..2266
    (D) OTHER INFORMATION: /label= 3'nos
        /note= "3' untranslated region containing the
        polyadenyla tion signal of the nopaline synthase gene of
        Agrobacteri um T-DNA"

(ix) FEATURE:
    (A) NAME/KEY: -
    (B) LOCATION: 2321..2345
    (D) OTHER INFORMATION: /label= LB
        /note= "T-DNA left border"

(xi) SEQUENCE DESCRIPTION: SEQ ID NO: 1:

```
AATTACAACG GTATATATCC TGCCAGTACT CGGCCGTCGA CCGCGGTACC C GGAATTCCA      60
ATCCCACCAA AACCTGAACC TAGCAGTTCA GTTGCTCCTC TCAGAGACGA A TCGGGTATT     120
CAACACCCTC ATACCAACTA CTACGTCGTG TATAACGGAC CTCATGCCGG T ATATACGAT    180
GACTGGGGTT GTACAAAGGC AGCAACAAAC GGTGTTCCCG GAGTTGCGCA T AAGAAGTTT    240
GCCACTATTA CAGAGGCAAG AGCAGCAGCT GACGCGTATA CAACAAGTCA G CAAACAGAT    300
AGGTTGAACT TCATCCCCAA AGGAGAAGCT CAACTCAAGC CCAAGAGCTT T GCGAAGGCC    360
CTAACAAGCC CACCAAAGCA AAAAGCCCAC TGCTCACGCT AGGAACCAAA A GGCCCAGCA    420
GTGATCCAGC CCCAAAAGAG ATCTCCTTTG CCCCGGAGAT TACAATGGAC G ATTTCCTCT    480
ATCTTTACGA TCTAGGAAGG AAGTTCGAAG GTGAAGGTGA CGACACTATG T TCACCACTG    540
ATAATGAGAA GGTTAGCCTC TTCAATTTCA GAAAGAATGC TGACCCACAG A TGGTTAGAG    600
AGGCCTACGC AGCAGGTCTC ATCAAGACGA TCTACCCGAG TAACAATCTC C AGGAGATCA    660
AATACCTTCC CAAGAAGGTT AAAGATGCAG TCAAAAGATT CAGGACTAAT T GCATCAAGA    720
ACACAGAGAA AGACATATTT CTCAAGATCA GAAGTACTAT TCCAGTATGG A CGATTCAAG    780
GCTTGCTTCA TAAACCAAGG CAAGTAATAG AGATTGGAGT CTCTAAAAAG G TAGTTCCTA    840
CTGAATCTAA GGCCATGCAT GGAGTCTAAG ATTCAAATCG AGGATCTAAC A GAACTCGCC    900
GTGAAGACTG GCGAACAGTT CATACAGAGT CTTTTACGAC TCAATGACAA G AAGAAAATC    960
TTCGTCAACA TGGTGGAGCA CGACACTCTG GTCTACTCCA AAAATGTCAA A GATACAGTC   1020
TCAGAAGACC AAAGGGCTAT TGAGACTTTT CAACAAAGGA TAATTTCGGG A AACCTCCTC   1080
GGATTCCATT GCCCAGCTAT CTGTCACTTC ATCGAAAGGA CAGTAGAAAA G GAAGGTGGC   1140
TCCTACAAAT GCCATCATTG CGATAAAGGA AAGGCTATCA TTCAAGATGC C TCTGCCGAC   1200
AGTGGTCCCA AAGATGGACC CCCACCCACG AGGAGCATCG TGGAAAAAGA A GACGTTCCA   1260
ACCACGTCTT CAAAGCAAGT GGATTGATGT GACATCTCCA CTGACGTAAG G GATGACGCA   1320
CAATCCCACT ATCCTTCGCA AGACCCTTCC TCTATATAAG GAAGTTCATT T CATTTGGAG   1380
AGGACACGCT GAAATCACCA GTCTCTCTCT ATAAATCTAT CTCTCTCTCT A TAACCATGG   1440
ACCCAGAACG ACGCCCGGCC GACATCCGCC GTGCCACCGA GGCGGACATG C CGGCGGTCT   1500
```

-continued

```
GCACCATCGT CAACCACTAC ATCGAGACAA GCACGGTCAA CTTCCGTACC G AGCCGCAGG    1560

AACCGCAGGA GTGGACGGAC GACCTCGTCC GTCTGCGGGA GCGCTATCCC T GGCTCGTCG    1620

CCGAGGTGGA CGGCGAGGTC GCCGGCATCG CCTACGCGGG CCCCTGGAAG G CACGCAACG    1680

CCTACGACTG GACGGCCGAG TCGACCGTGT ACGTCTCCCC CCGCCACCAG C GGACGGGAC    1740

TGGGCTCCAC GCTCTACACC CACCTGCTGA AGTCCCTGGA GGCACAGGGC T TCAAGAGCG    1800

TGGTCGCTGT CATCGGGCTG CCCAACGACC CGAGCGTGCG CATGCACGAG G CGCTCGGAT    1860

ATGCCCCCCG CGGCATGCTG CGGGCGGCCG GCTTCAAGCA CGGGAACTGG C ATGACGTGG    1920

GTTTCTGGCA GCTGGACTTC AGCCTGCCGG TACCGCCCCG TCCGGTCCTG C CCGTCACCG    1980

AGATCTGATC TCACGCGTCT AGGATCCGAA GCAGATCGTT CAAACATTTG G CAATAAAGT    2040

TTCTTAAGAT TGAATCCTGT TGCCGGTCTT GCGATGATTA TCATATAATT T CTGTTGAAT    2100

TACGTTAAGC ATGTAATAAT TAACATGTAA TGCATGACGT TATTTATGAG A TGGGTTTTT    2160

ATGATTAGAG TCCCGCAATT ATACATTTAA TACGCGATAG AAAACAAAAT A TAGCGCGCA    2220

AACTAGGATA AATTATCGCG CGCGGTGTCA TCTATGTTAC TAGATCGGGA A GATCCTCTA    2280

GAGTCGACCT GCAGGCATGC AAGCTTAGAT CCATGGAGCC ATTTACAATT G AATATATCC    2340

TGCCG                                                                 2345
```

(2) INFORMATION FOR SEQ ID NO: 2:

(i) SEQUENCE CHARACTERISTICS:
        (A) LENGTH: 1086 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "coding region of the bar (ix) FEATURE:
        (A) NAME/KEY: CDS
        (B) LOCATION: 1..233
        (D) OTHER INFORMATION: /product= "phosphinotricin
            acetyltrans ferase (N-terminal half)"

(ix) FEATURE:
        (A) NAME/KEY: intron
        (B) LOCATION: 234..769
        (D) OTHER INFORMATION: /standard_name= "adh1 intron"

(ix) FEATURE:
        (A) NAME/KEY: CDS
        (B) LOCATION: 770..1086
        (D) OTHER INFORMATION: /product= "phosphinotricin acetyl
            transferase (c-terminal half)"

(xi) SEQUENCE DESCRIPTION: SEQ ID NO: 2:

```
ATGGACCCAG AACGACGCCC GGCCGACATC CGCCGTGCCA CCGAGGCGGA C ATGCCGGCG     60

GTCTGCACCA TCGTCAACCA CTACATCGAG ACAAGCACGG TCAACTTCCG T ACCGAGCCG    120

CAGGAACCGC AGGAGTGGAC GGACGACCTC GTCCGTCTGC GGGAGCGCTA T CCCTGGCTC    180

GTCGCCGAGG TGGACGGCGA GGTCGCCGGC ATCGCCTACG CGGGCCCCTG G AAAGGTCCG    240

CCTTGTTTCT CCTCTGTCTC TTGATCTGAC TAATCTTGGT TTATGATTCG T TGAGTAATT    300

TTGGGGAAAG CTTCGTCCAC AGTTTTTTTT TCGATGAACA GTGCCGCAGT G GCGCTGATC    360

TTGTATGCTA TCCTGCAATC GTGGTGAACT TATGTCTTTT ATATCCTTCA C TACCATGAA    420

AAGACTAGTA ATCTTTCTCG ATGTAACATC GTCCAGCACT GCTATTACCG T GTGGTCCAT    480

CCGACAGTCT GGCTGAACAC ATCATACGAT ATTGAGCAAA GATCTATCTT C CCTGTTCTT    540
```

```
TAATGAAAGA CGTCATTTTC ATCAGTATGA TCTAAGAATG TTGCAACTTG C AAGGAGGCG        600

TTTCTTTCTT TGAATTTAAC TAACTCGTTG AGTGGCCCTG TTTCTCGGAC G TAAGGCCTT        660

TGCTGCTCCA CACATGTCCA TTCGAATTTT ACCGTGTTTA GCAAGGGCGA A AAGTTTGCA        720

TCTTGATGAT TTAGCTTGAC TATGCGATTG CTTTCCTGGA CCCGTGCAGC T AGGAACGCC        780

TACGACTGGA CGGCCGAGTC GACCGTGTAC GTCTCCCCCC GCCACCAGCG G ACGGGACTG        840

GGCTCCACGC TCTACACCCA CCTGCTGAAG TCCCTGGAGG CACAGGGCTT C AAGAGCGTG        900

GTCGCTGTCA TCGGGCTGCC CAACGACCCG AGCGTGCGCA TGCACGAGGC G CTCGGATAT        960

GCCCCCCGCG GCATGCTGCG GGCGGCCGGC TTCAAGCACG GGAACTGGCA T GACGTGGGT       1020

TTCTGGCAGC TGGACTTCAG CCTGCCGGTA CCGCCCCGTC CGGTCCTGCC C GTCACCGAG       1080

ATCTGA                                                                  1086

(2) INFORMATION FOR SEQ ID NO: 3:

(i) SEQUENCE CHARACTERISTICS:
        (A) LENGTH: 108 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "T-DNA of pGSV8"

(ix) FEATURE:
        (A) NAME/KEY: -
        (B) LOCATION: 1..25
        (D) OTHER INFORMATION: /label= RB
            /note= "right border sequence from the T-DNA of pGSV8"

(ix) FEATURE:
        (A) NAME/KEY: -
        (B) LOCATION: 26..83
        (D) OTHER INFORMATION: /label= MCS
            /note= "Multiple cloning site"

(ix) FEATURE:
        (A) NAME/KEY: -
        (B) LOCATION: 84..108
        (D) OTHER INFORMATION: /label= LB
            /note= "left border sequence from the T-DNA of pGSV8"

(xi) SEQUENCE DESCRIPTION: SEQ ID NO: 3:

AATTACAACG GTATATATCC TGCCAGTACT CGGCCGTCGA CCGCGGTACC C GGAATTCCG         60

GGGAAGCTTA GATCCATGGA GCCATTTACA ATTGAATATA TCCTGCCG                     108

(2) INFORMATION FOR SEQ ID NO: 4:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide VG40"

(xi) SEQUENCE DESCRIPTION: SEQ ID NO: 4:

GCCAAAAAGT TTGATCTAGA GCATTTTCG                                           29

(2) INFORMATION FOR SEQ ID NO: 5:

(i) SEQUENCE CHARACTERISTICS:
        (A) LENGTH: 33 base pairs
        (B) TYPE: nucleic acid
```

```
        (C) STRANDEDNESS: single
        (D) TOPOLOGY: linear (ii) MOLECULE TYPE: other nucleic acid
        (A) DESCRIPTION: /desc = "oligonucleotide VG41"

(xi) SEQUENCE DESCRIPTION: SEQ ID NO: 5:

GCGACCCCGC TAGCTTAAAC AAAGCTTATC TCC                                       33
```

TRANSFORMATION METHOD FOR PLANTS

CROSS REFERENCE TO RELATED APPLICATIONS

This application is a divisional, of application Ser. No. 09/026,673, filed Feb. 20, 1998, which is a continuation of Ser. No. 08/808,988, filed Feb. 20, 1997, which was converted provisional application 60/135,507, on Feb. 20, 1998.

BACKGROUND TO THE INVENTION (i) Field of the Invention

The present invention relates to tissue cultures of plant cells, particularly monocotyledonous plant cells, quite particularly corn, rice, wheat and barley cells, and improved techniques to obtain genetically transformed plant cells and plants.

(ii) Description of the Related Art

Over the years many techniques for the genetic transformation of plants have been developed. These methods have as their ultimate goal the obtaining of a transgenic plant, in which all cells contain a foreign DNA comprising a gene of interest (the so-called transgene) stably integrated in their genome, particularly their nuclear genome.

Transformation is a complex process which always involves the contacting of starting cells with a DNA, usually a DNA comprising foreign gene(s) of interest. The contacting of the cells with the DNA is carried out under conditions that promote the uptake of the DNA by the cells and the integration of the DNA, including the gene(s) of interest into the genome of the cell.

Starting cells for transformation are usually cells that have been cultured in vitro for some time. After contacting the cells with the DNA, the transformed cells generally need to be cultured in vitro for a certain period in order to separate the transformed cells from the non-transformed cells and to regenerate transformed plants from the transformed cells.

Different plant transformation methods have been described and can be classified into direct DNA transfer methods (e.g. electroporation, PEG-mediated DNA uptake, biolistics) or Agrobacterium-mediated DNA transfer. Vasil (1994) and Christou (1994) have reviewed available plant transformation methods for cereals. Agrobacterium-mediated DNA transfer is one of the most efficient means of DNA transfer into plant cells, and requires probably the least technological hardware of the different transformation methods. Also quantitatively, the transformed plants obtained by Agrobacterium-mediated DNA transfer are superior, in comprising a smaller number of transgenes inserted at different positions in the chromosome, and in that aberrant transgenes have a lower occurrence. Agrobacterium-mediated DNA transformation of plants is based on the capacity of certain Agrobacterium strains to introduce a part of their Ti-plasmid, i.e. the T-DNA, into plant cells and to integrate this T-DNA into the nuclear genome of the cells. It was found that the part of the Ti-plasmid that is transferred and integrated is delineated by specific DNA sequences, the so-called left and right T-DNA border sequences and that the natural T-DNA sequences between these border sequences can be replaced by foreign DNA (European Patent Publication "EP" 116718; Deblaere et al., 1987).

Agrobacterium-mediated transformation of monocotyledonous plants has been reported several times (see infra). The applicability of the reported methods has been limited however, to specific species or genotypes, or required the use of specific tissues, or specialized Agrobacterium strains. For most of the reported methods, transformation efficiency can still largely be improved.

Hooykaas-Van Slogteren et al. (1984), describes the detection of Ti-plasmid gene expression in two monocot species (*Chlorophytum capense* and *Narcissus* cv 'Paperwhite') infected with tumorogenic Agrobacterium strains.

Hernalsteens et al. (1984) and Bytebier et al. (1 987), describe transformation of *Asparagus officinalis* using natural *Agrobacterium tumefaciens* isolates, as well as Agrobacterium tumefaciens strains comprising a non-oncogenic T-DNA.

U.S. Pat. No. 5,164,310 describes a method to transform plants (comprising corn and wheat) by inoculating excised and cultured shoot apices of the plants with *Agrobacterium tumefaciens*.

U.S. Pat. Nos. 5,187,073 and 5,177,010 describe a method of producing transformed Graminaea (corn) comprising making a wound in a seedling in an area of the seedling containing rapidly dividing cells and inoculating the wound with vir+ *Agrobacterium tumefaciens*.

PCT patent publication WO 92/09696 describes the use of compact embryogenic callus (i.e. Type I callus in corn) and immature embryos (wounded either mechanically or enzymatically) of monocotyledonous plants (e.g. corn and rice) as starting material for transformation procedures.

EP 0604662 A1 describes a method of transforming cultured tissues of a monocotyledon under or after dedifferentiation with a bacterium of the genus Agrobacterium containing desired genes. EP 0672752 A1 describes a method of transforming a scutulum of a non-dedifferentiated immature embryo of a monocotyledon with an Agrobacterium. Both applications describe the use of Agrobacterium strains having a plasmid containing a DNA fragment originating from the virulence region of Ti-plasmid pTiBo542 in addition to the Ti or Ri plasmid.

Raineri et al. (1990) describes transformation of embryo-derived cultures of two rice cultivars, wounded in the scutellar region, using an Agrobacterium mediated gene transfer system.

Chan et al. (1993) describes a method to transform immature embryos of rice that have been cultured for 2 days in the presence of 2,4-dichlorophenoxy acetic acid ("2,4-D") by inoculation with Agrobacterium strains on a medium containing potato suspension culture cells.

Mooney et al., (1991) describes a method for Agrobacterium-mediated introduction of a kanamycin-resistant gene into enzyme-treated embryos of wheat.

Induction of the vir genes of Ti plasmids or helper plasmids of Agrobacteria strains by incubation of the bacteria with acetosyringone prior to cocultivation to enhance transformation, and addition of acetosyringone during cocultivation of the plant cells with the bacteria has been reported (Van Wordragen and Dons, 1992; Jacq et al., 1993; James et al., 1993).

Guivarc'h et al. (1993) describes improvement of transient Agrobacterium-mediated transformation of carrot root discs by a short pretreatment of these discs for ten minutes with acetosyringone.

SUMMARY AND OBJECTS OF THE INVENTION

Provided is a process for integrating a DNA fragment into the genome of a cell of a monocotyledonous plant, particularly corn, rice, wheat or barley, comprising the steps of:

1) incubating, prior to the contacting with the DNA fragment, a culture of untransformed monocotyledonous plant cells on a medium comprising a plant phenolic compound, particularly a plant phenolic compound selected from the group of acetosyringone, -hydroxy-acetosyringone, sinapinic acid, syringic acid, ferulic acid, catechol, p-hydroxybenzoic acid, β-resorcylic acid, protocatechuic acid, pyrrogallic acid, gallic acid and vanillin, for a period of time sufficient to stimulate the cell division and enhance the competence for integration of foreign DNA, preferably for approximately 1 to 10 days, particularly for approximately 4 to 5 days; and 2) contacting the untransformed cells with the DNA fragment under conditions in which the DNA fragment is taken up by the untransformed cells and is stably integrated in the genome of the untransformed cells, to generate transformed cells, particularly by means of electroporation, direct gene transfer using polyethyleneglycol, bombardment with DNA-coated microprojectiles or by co-cultivation with an Agrobacterium strain comprising the DNA fragment.

Optionally, the transformed cells can be regenerated into a transgenic monocotyledonous plant.

Further provided is a process for integrating a DNA fragment into the genome of a cell of a corn plant, comprising the steps of:

incubating, prior to the contacting with the DNA fragment, a type I callus, preferably a type I callus which has been cut into fragments, particularly fragments having a maximum length of 0.5 to 5 mm, with a plant phenolic compound, particularly a plant phenolic compound selected from the group of acetosyringone, -hydroxy-acetosyringone, sinapinic acid, syringic acid, ferulic acid, catechol, p-hydroxybenzoic acid, β-resorcylic acid, protocatechuic acid, pyrrogallic acid, gallic acid and vanillin, for a period of time sufficient to stimulate the cell division and enhance the competence for integration of foreign DNA, preferably for approximately 1 to 10 days, particularly for approximately 4 to 5 days; or incubating, prior to the contacting with the DNA fragment, a type I callus, on a medium comprising a plant phenolic compound for a period of time sufficient to stimulate the cell division and enhance the competence for integration of foreign DNA prior to cutting the type I callus in fragments, particularly fragments having a maximum length of 0.5 to 5 mm; and 2) contacting the untransformed cells with the DNA fragment under conditions in which the DNA fragment is taken up by the untransformed cells and is stably integrated in the genome of the untransformed cells, to generate transformed cells, particularly by means of electroporation, direct gene transfer using polyethylene-glycol, bombardment with DNA-coated microprojectiles or by co-cultivation with an Agrobacterium strain comprising the DNA fragment.

Also provided is a method of increasing the frequency of stable transformation in monocotyledonous plants in the presence of a plant phenolic compound, wherein the plant phenolic compound is included in the media in which plant cells are cultured prior to contacting the cultured tissue with the foreign DNA.

Further provided are plant media compositions comprising at least two plant phenolic compounds.

DETAILED DESCRIPTION OF PREFERRED EMBODIMENTS

The invention is based on the initial observation that cultivation of plant calli, particularly corn calli, quite particularly finely cut pieces of type I calli of corn, on a cultivation medium comprising plant phenolic compounds, such as acetosyringone, for about 5 days, greatly stimulated cell division, yielding reproducibly calli with enhanced competence for integration in the genome of foreign DNA transferred into the cell via Agrobacterium mediated transformation, as reflected by the number of transformed cells and plants that were recovered under standardized conditions.

"Untransformed cells" as used herein, refers to cells which have not been contacted with the particular DNA fragment which will be used when applying the method of the invention. It goes without saying that such cells may also be derived from a transgenic plant or plant tissue, previously transformed with a different or similar DNA fragment.

The "efficiency of transformation" or "frequency of transformation" as used herein can be measured by the number of transformed cells (or transgenic organisms grown from individual transformed cells) that are recovered under standard experimental conditions (i.e. standardized or normalized with respect to amount of cells contacted with foreign DNA, amount of delivered DNA, type and conditions of DNA delivery, general culture conditions etc.) For example, when callus fragments are used as starting material for transformation, the frequency of transformation can be expressed as the number of transgenic plant lines obtained per 100 callus pieces transformed. Transformation frequencies of about 1% or higher were obtained using the method of the invention.

A transgenic "plant line" as used herein, consists of a group of transgenic plants, originating from one unit of cultured cells, e.g. one transformed callus piece, obtained during the regeneration process. In general, plants from one plant line are genetically identical, and originate from one transformation event, thus comprising the same transgenes integrated at the same genomic positions.

However, individual plants from one plant line as herein defined can originate from independent transformation events, particularly when using Agrobacterium-mediated DNA transfer, and may thus differ from one another. When transformation frequencies are expressed by the number of plant lines/100 initial callus pieces, it may be that the actual transformation frequencies (transformation events/100 initial callus pieces) are even higher.

"Plant phenolic compounds" or "plant phenolics" suitable for the invention are those isolated substituted phenolic molecules which are capable to induce a positive chemotactic response, particularly those who are capable to induce increased vir gene expression in a Ti-plasmid containing Agrobacterium sp., particularly a Ti-plasmid containing *Agrobacterium tumefaciens*. Methods to measure chemotactic responses towards plant phenolic compounds have been described by Ashby et al. (1988) and methods to measure induction of vir gene expression are also well known (Stachel et al., 1985; Bolton et al. 1986).

It is thought that the beneficial effect on transformation efficiency by incubation of the plant tissues on a medium containing a plant phenolic compound is largely due to the induction of cell division and the enhancement of the competence for incorporation of foreign DNA into the genome of the plant cell. It is known that most monocotyledonous plants, particularly the cereals, upon wounding do not respond in a similar way as observed in most dicotyledonous plants (Potrykus, 1991). It is thought that the exogenous supply of plant phenolic compounds may trigger a wound-like response, particularly when applied to monocotyledonous plants. The induction of vir-genes by residual concentrations of plant phenolic compounds taken up by the pretreated plant tissues, when using Agrobacterium-mediated DNA transfer, may also affect transformation efficiency but it is thought that this effect is less important. Indeed, a similar enhancement of transformation was also observed when using direct DNA transfer methods.

Preferred plant phenolic compounds are those found in wound exudates of plant cells. One of the best known plant phenolic compounds is acetosyringone, which is present in a number of wounded and intact cells of various plants, albeit in different concentrations. However, acetosyringone (3,5-dimethoxy-4-hydroxyacetophenone) is not the only plant phenolic which can induce the expression of vir genes. Other examples are -hydroxy-acetosyringone, sinapinic acid (3,5 dimethoxy-4-hydroxycinnamic acid), syringic acid (4-hydroxy-3,5 dimethoxybenzoic acid), ferulic acid (4-hydroxy-3-methoxycinnamic acid), catechol (1,2-dihydroxybenzene), p-hydroxybenzoic acid (4-hydroxybenzoic acid), βresorcylic acid (2,4 dihydroxybenzoic acid), protocatechuic acid (3,4-dihydroxybenzoic acid), pyrrogallic acid (2,3,4-trihydroxybenzoic acid), gallic acid (3,4,5-trihydroxybenzoic acid) and vanillin (3-methoxy-4-hydroxybenzaldehyde), and these phenolic compounds are known or expected to be able to replace acetosyringone in the cultivation media with similar results. As used herein, the mentioned molecules are referred to as plant phenolic compounds.

Plant phenolic compounds can be added to the plant culture medium either alone or in combination with other plant phenolic compounds. A particularly preferred combination of plant phenolic compounds comprises at least acetosyringone and p-hydroxybenzoic acid, but it is expected that other combinations of two, or more, plant phenolic compounds will also act synergistically in enhancing the transformation efficiency.

Moreover, certain compounds, such as osmoprotectants (e.g. L-proline preferably at a concentration of about 700 mg/L or betaine), phytohormes, (inter alia NAA), opines, or sugars, are expected to act synergistically when added in combination with plant phenolic compounds.

Although the invention is particularly useful for improved Agrobacterium-mediated DNA transfer to plant cells, particularly corn cells, plant cell cultures, particularly of monocotyledonous plants, which have been pretreated with plant phenolics can also be employed to obtain improved efficiency of transformation using direct DNA transfer methods, such as PEG mediated DNA transfer, particle bombardment or electroporation. Basically, the present invention thus provides an improvement of existing procedures for the genetic transformation of plant cells, particularly monocotyledonous plant cells, quite particularly corn cells, by including in the medium in which such cells are cultured, a plant phenolic compound such as acetosyringone, for a defined period of time. In particular, the plant cells or plant tissues are cultivated for 5 days on a culture medium containing acetosyringone (100–200 $\mu$M) prior to the moment at which the cells are contacted with the foreign DNA, which is introduced into the cells either directly via electroporation, PEG mediated DNA transfer or particle bombardment, or preferably via Agrobacterium mediated DNA transfer.

In a preferred embodiment, the method of the invention is used to improve the transformation frequency of Agrobacterium-mediated DNA transfer to plant cells, particularly corn cells.

In many conventional procedures for genetic transformation of plant cells, particularly monocotyledonous plant cells, cultured cells, tissues or explants will be used as starting materials and cells in such cultures will be contacted with foreign DNA comprising at least one gene of interest (i.e. the transgene) under conditions that will promote the uptake of foreign DNA into the genome of the cells. Suitable media for the cultivation of plant cells, tissues, organs or explants are generally known in the art. Preferred plant culture media are defined culture media for which the chemical composition is known.

In one embodiment of the invention, it is preferred that the plant phenolic compound, particularly acetosyringone is added to the medium for a period of about 4 to 5 or 6 days, preferably at least about 5 days, prior to contacting the cells with the foreign DNA. The exact period in which the cultured cells are incubated in the medium containing the plant phenolic compound such as acetosyringone, is believed not to be critical but should probably not exceed 2 weeks. It appears that 1–10 days, particularly 3–7 days, is an optimal period and best results were obtained with an incubation period of approximately 4 to 5 or 6 days prior to the contacting time. Generally, it is believed that about 5 days is a useful period for the plant phenolic compound to be added to the culture medium prior to the contacting time.

It should be noted that the cultured tissue might exhibit browning or even limited necrosis after incubation on the plant phenolic comprising medium, particularly when gallic acid is included in the culture medium. Yet, improved transformation efficiency can be obtained using these cultured cells, tissue or explants.

The concentration of the plant phenolic compound in the medium is also believed to have an effect on the development of competence for integrative transformation, which varies depending on the nature of the cells (species, tissue explant, general culture conditions, etc.). However, within certain concentration ranges, the effect is minimal, especially when the cultured cells are not incubated for longer than 7 days. The optimal concentration range of plant phenolic compounds in the medium may vary depending on the species from which the tissue, cell or cell culture is derived, or on the type of tissue used, but it is expected that about 100 $\mu$M–200 $\mu$M is a suitable concentration for many purposes (e.g. for use with material derived from corn). The optimal concentration may also depend on the nature of the specific plant phenolic compound used, particularly on its cell-division promoting strength.

It was found for instance that the optimal concentration for acetosyringone is approximately 200 $\mu$M, but concentrations as low as approximately 25 $\mu$M can be used to obtain a good effect on transformation efficiency. Likewise, it is expected that higher concentrations up to approximately 400 $\mu$M will yield similar effects.

Comparable concentrations apply to other plant phenolic compounds, and optimal concentrations can be established easily by experimentation in accordance with this invention.

As stated above, plant transformation procedures generally include the culturing of cells, cell cultures, tissue or explants prior to contacting the cultured tissue with the foreign DNA. Several tissues have been described as starting material for the transformation procedures, including but not limited to dry seeds, immature embryos, immature inflorescenses, anthers, microspores, scutella, nodes, young leaf bases, hypocotyl explants, roots (particularly root tips), compact embryogenic calli (e.g. type I in corn), friable embryogenic calli (e.g. type II in corn), suspension cultures, cultures of suspended cell aggregates, somatic embryos and shoot apexes. It is expected that inclusion of plant phenolic compounds, particularly acetosyringone, in the medium on which these tissues, cells, cell cultures or explants are incubated prior to contact with the foreign DNA, will improve the transformation efficiency, particularly when using Agrobacterium-mediated transformation.

It is clear that whenever "incubating on a (plant) medium" is used, the medium can either be liquid or solid. In the framework of the inventions the plant media comprise at least one plant phenolic compound.

It goes without saying that, where the ultimate goal of the transformation procedure is to regenerate transgenic plants, particularly phenotypically normal plants, the starting material should be capable of regeneration, as widely documented in the prior art.

In a particularly preferred embodiment, transformation competent plant cells, preferably Agrobacterium transformation competent plant cells are generated by incubation of compact regenerable callus, such as corn type I callus on a medium comprising a plant phenolic, preferably acetosyringone. To this end, the compact callus is divided by cutting into smaller fragments. The resulting callus should comprise, wholly or at least in part, the regenerable (e.g. the embryogenic) sectors or parts of the callus. The callus fragments also preferably have an average maximum length of 0.5 to 5 mm, particularly 1 to 2 mm, more particularly 1.25 to 1.75 mm and preferably have a minimum length of about 0.1 mm. It is nevertheless feasible to use larger type I callus fragments, of up to about 1 cm. After cultivation on the plant phenolic comprising media, the calli can be contacted with the foreign DNA, preferably with the Agrobacteria comprising the foreign DNA, without further wounding or enzymatic pretreatment.

Alternatively, the compact callus can be incubated, without wounding (i.e. cutting), on a medium comprising a plant phenolic compound, and subsequently be wounded, i.e. cut in smaller fragments, particularly fragments having the above-mentioned dimensions prior to the contacting step.

In another embodiment, transformation competent, particularly Agrobacterium-transformation competent cells, are generated by incubation of immature embryos, preferably corn immature embryo's on a medium comprising a plant phenolic, preferably acetosyringone. In this regard, for plants such as corn, it is preferred that the immature embryos have a maximum length of about 0.5 to 2 mm, preferably 0.5 to 1.5 mm, even though smaller embryos with lengths of 0.5 to 1 mm can be used. After cultivation on the plant phenolic comprising media, the immature embryos can be contacted with the foreign DNA, preferably with the Agrobacteria comprising the foreign DNA without further wounding or enzymatic pretreatment.

It has been found that using this invention, different genotypes of corn are amenable to Agrobacterium-mediated DNA transfer, particularly corn, PHH [(Pa91xH99)xH99], Pa91 HE89 or PHP[(Pa91xH99)xPa91]. It is therefore expected that the invention can be employed without genotype limitations, particularly for transformation of corn.

Preculturing the plant cells, particularly corn cells according to the invention increases the transformation efficiency of Agrobacterium mediated DNA transfer, and it is expected that this effect is independent of the chromosomal background of the Agrobacterium host, the type of Ti-plasmid, helper-plasmid or T-DNA vector used. The method of invention thus expands the range of Agrobacterium strains which can be used efficiently.

Particularly preferred bacterial chromosomal backgrounds are provided by A. tumefaciens C58C1 (Van Larebeke et al., 1974), A136 (Watson et al., 1975) or LBA4011 (Klapwijk et al., 1980).

In a preferred embodiment, the Agrobacterium strain used to transform the plant tissue precultured with the plant phenolic compound contains a L,L-succinamopine type Ti-plasmid, preferably disarmed, such as pEHA101.

In another preferred embodiment, the Agrobacterium strain used to transform the plant tissue precultured with the plant phenolic compound contains an octopine-type Ti-plasmid, preferably disarmed, such as pAL4404. Generally, when using octopine-type Ti-plasmids or helper plasmids, it is preferred that the virF gene be deleted or inactivated (Jarschow et al., 1991).

The method of the invention can also be used in combination with particular Agrobacterium strains, to further increase the transformation efficiency, such as Agrobacterium strains wherein the vir gene expression and/or induction thereof is altered due to the presence of mutant or chimeric virA or virG genes (e.g. Hansen et al., 1994; Chen and Winans 1991; Scheeren-Groot et al., 1994).

In another embodiment, Agrobacterium strains comprising extra virG gene copies, particularly the so-called super virG gene derived from pTiBo542, preferably linked to a multiple-copy plasmid, can be used to further increase the transformation efficiency.

In yet another embodiment of the invention, the used Agrobacterium strains comprise an extra virB11 gene copy, particularly the virB11 gene derived from pTiBo542, which is expressed in Agrobacterium. This can be accomplished preferably by providing a chimeric gene comprising the virB11 coding region operably linked to a promoter capable of expression in Agrobacterium, such as an isolated virB promoter, without other intervening coding regions of the virB operon.

Agrobacterium cells to be co-cultivated with the plant cells, particularly with the corn cells, can be either preincubated with acetosyringone or another plant phenolic compound, as known by the person skilled in the art, or used directly after isolation from their culture medium. Particularly suited induction conditions for *Agrobacterium tumefaciens* have been described by Vernade et al. (1988).

The method of the present invention can in principle be used to transform plant cells, particularly corn cells, with any foreign DNA. Generally the foreign DNA comprises at least one gene of interest comprising 1) a promoter region with a promoter capable of directing transcription of DNA into a RNA in cells of the eucaryotic, e.g. plant, species that is to be transformed and 2) a coding region coding for a RNA (e.g. an antisense RNA or a ribozyme) or protein. Most often the gene of interest will also comprise 3) a 3' untranslated region of a eucaryotic gene containing a polyadenylation signal. The promoter can be selected to direct expression in selected tissues of the eucaryotic organism. For instance promoters are known that direct expression selectively in stamen cells of a plant (e.g. tapetum) and such promoters have been used to produce male sterile plants and other plants useful for producing hybrids (EP 344029; EP 412911; WO 9213956; WO 9213957; Mariani et al., 1990,; Mariani et al., 1992).

The foreign DNA used in the method of this invention preferably also comprises a selectable marker gene the expression of which allows the selection of transformed cells (or organisms) from non-transformed cells (or organisms). Such selectable marker gene generally encodes a protein that confers to the cell resistance to an antibiotic or other chemical compound that is normally toxic for the cells.

In plants the selectable marker gene may thus also encode a protein that confers resistance to an herbicide, such as an herbicide comprising a glutamine synthetase inhibitor (e.g. phosphinothricin) as an active ingredient. An example of such genes are genes encoding phosphinothricin acetyl transferase such as the sfr or sfrv genes (EP 242236; EP 242246; De Block et al., 1987).

This invention thus provides a rapid, efficient and reproducible method for increasing the transformation efficiency of DNA transfer, particularly Agrobacterium-mediated DNA transfer of plant cells, particularly of monocotyledonous plant cells, quite particularly of corn cells, but also of rice, wheat or barley cells. Moreover, Agrobacterium-mediated transformation methods yield a higher number of transgenic plants, particularly corn plants, with a limited number of transgene copies, particularly with one transgene copy, integrated in the genome of their cells, than direct gene transfer methods do. In addition, transgenic plants, particularly transgenic corn plants, obtained by Agrobacterium-mediated transformation, which have more than one copy of the transgene integrated in their genome, frequently produce progeny plants wherein the different copies of the transgene are inherited independently, allowing segregation of the different transgene copies in the descendant plants. It is therefore expected that a larger proportion of "elite" transgenic plants with the desired characteristics, will be found in a population of transgenic plants obtained by the transformation methods of the invention than in a population of transgenic plants obtained by direct gene transfer methods. Although the invention is particularly useful for monocotyledonous plants, it is expected that similar results will be obtained when using cultured cells from dicotylodonous plants as the starting material for the method of the invention.

The following Examples describe the methods of the invention in detail. Unless stated otherwise in the Examples, all recombinant DNA techniques are carried out according to standard protocols as described in Sambrook et al. (1989) *Molecular Cloning: A Laboratory Manual*, Second Edition, Cold Spring Harbor Laboratory Press, NY and in Volumes 1 and 2 of Ausubel et al. (1994) Current *Protocols in Molecular Biology, Current Protocols*, USA. Standard materials and methods for plant molecular work are described in *Plant Molecular Biology Labfax* (1993) by R. D. D. Croy, jointly published by BIOS Scientific Publications Ltd (UK) and Blackwell Scientific Publications, UK.

In the examples and in the description of the invention, reference is made to the following sequences of the Sequence Listing:

SEQ ID No. 1: nucleotide sequence of the T-DNA of pGVS71

SEQ ID No. 2: nucleotide sequence of the coding region of the bar gene comprising the adh1 intron SEQ ID No. 3: nucleotide sequence of the T-DNA of pGVS8

SEQ ID No. 4: nucleotide sequence of the oligonucleotide VG40

SEQ ID No. 5: nucleotide sequence of the oligonucleotide VG41

Experimental

Media, Plasmids and Bacterial Strains Used in the Examples 1.1. Media

Throughout the Examples, the following media for plant tissue culture were used:

Mahi1VII: N6 medium. (Chu et al. 1975) supplemented with 100 mg/L casein hydrolysate, 6 mM L-proline, 0.5 g/L 2-(N-morpholino)ethanesulfonic acid (MES), 0.2 M mannitol, 2% sucrose, 1 mg/L 2,4-dichlorophenoxy acetic acid (2,4-D), 2.5 g/L Gelrite, adjusted to pH 5.8.

LSIDhy1.5VII: MS salts (Murashige and Skoog, 1968) supplemented with 0.5 mg/L nicotinic acid, 0.5 mg/L pyridoxine.HCl, 1 mg/L thiamine.HCl, 100 mg/L myo-inositol, 6 mM L-proline, 0.5 g/L MES, 20 g/L sucrose, 10 g/L glucose, 1.5 mg/L 2,4-D, 2.5 g/L Gelrite, adjusted to pH 5.2.

LSI: MS salts, supplemented with vitamins as in LSIDhy 1.5VII, 1 g/L casamino acids, 0.2 M sucrose, 0.2 M glucose, 1.5 mg/L 2,4-D, 2.5 g/L Gelrite, adjusted to pH 5.2.

Ahx1.5VIIp500ino1000ppT10: MS salts, supplemented with 1000 mg/L myo-inositol, 0.5 g/L MES, 30 g/L sucrose 10 g/L glucose, 1.5 mg/L 2,4-D, 2.5 g/L Phytagel, 10 mg/L glufosinate-ammonium, 500 mg/L carbenicillin, adjusted to pH 5.8.

Mh1VIIp500ppT5: N6 medium supplemented with 0.5 g/L MES, 20 g/L sucrose, 1 mg/L 2,4D, 5 mg/L glufosinate-ammonium, 500 mg/L carbenicillin, adjusted to pH 5.8.

A37VIIp500ppT2: MS medium supplemented with 0.5 g/L MES, 30 g/L sucrose, 5 mg/L zeatin, 2.5 g/L Phytagel, 2 mg/L glufosinate-ammonium, 500 mg/L carbenicillin, adjusted to pH 5.8.

LSIIDhy1.5XI idem to LSIDhy1.5VII medium, but wherein the 6 mM L-proline has been replaced by 1 g/L casaino acids and the 2.5 g/L Gelrite has been replaced by 0.5 % agarose BRL Ultra Pure.

A6%VIIp500ppT2 MS medium supplemented with 0.5 g/L MES, 60 g/L sucrose, 2.5 g/L Phytagel, 2 mg/L Glufosinate-ammonium, 500 mg/L carbenicillin, adjusted to pH 5.8.

1.2. T-DNA Vectors

Throughout the Examples, the following T-DNA vectors were used:

pGSV71: is a T-DNA vector derived from pGSC1700 (Cornelissen and Vandewiele, 1989) differing by the absence of the β-lactamase gene and the presence of the T-DNA characterized by the sequence of SEQ ID No. 1. pGVS71 comprises the selectable chimeric bar marker gene, operably linked to a CaMV35S promoter and the 3' end of the nopaline synthase gene.

pTCO114: is a T-DNA vector, similar to pGSV71, comprising a T-DNA wherein the coding sequence of the bar gene (nucleotide sequence from SEQ ID No. 1 from nucleotide position 1437 to nucleotide position 1988) has been replaced by the sequence of a bar gene comprising an intron from the adh1 gene from corn (nucleotide sequence from SEQ ID No. 2)

pTCO121: a T-DNA vector carrying the extra virG gene from pTiBo542 comprised on an about 1.3 kb BglII-SphI fragment, derived from pTiBo542. The T-DNA is essentially similar to that of pTCO114. The vector was constructed in the following way:

An about 1.3 kb BglII-SphI fragment was purified from pCNL2 (Liu et al. 1992). This fragment comprises the 3' end of the virB operon, the complete virG gene and the 3' end of the virB operon from pTiBo542. The fragment was blunt-ended by treatment with T4 polymerase and ligated to XbaI-linearized, Klenow-treated pGSV8, yielding pGSV15. pGSV8 is a T-DNA vector derived from pGSC1700 (Cornelissen and Vandewiele, 1989) differing by the absence of the β-lactamase gene and the presence of the T-DNA characterized by the sequence of SEQ ID No. 3. In a next step a T-DNA carrying the chimeric selectable bar marker was introduced in pGSV15. To this end, the about 1.2 kb EcoRI-BstEII fragment of pGSV15 (EcoRI site is within the T-DNA of pGSV15), was replaced by the about 4 kb EcoRI-BstEII fragment from pTCO114 which comprises the T-DNA (except for the right border), resulting in pTCO121.

pVE200: a T-DNA vector carrying the same T-DNA as pTCO121, and a similar pTiBo542 fragment comprising the 3' end of the virB operon (including the virB11 open reading frame), the complete virG gene and the 3' end of the virC operon, but wherein the 3' end of the virB operon, is operably linked (i.e. preceded) by a PCR-amplified virB promoter fragment. The vector was constructed in the following way:

a virB promoter fragment was amplified by standard polymerase chain reaction using the primers VG40 (SEQ ID No. 4) and VG41 (SEQ ID No. 5) and total DNA from A348(pSM30) (Stachel and Nester, 1986) as template. The resulting fragment of about 390 bp (corresponding essentially to the sequence of EMBL Accession No. J03216 from nucleotide 475 to nucleotide 764) comprises a virB promoter described by Das et al., (1986) was digested with XbaI and NheI and ligated to XbaI linearized pCNL2 (Liu et al., 1992), resulting in pVE194. In pVE194, the 3' end of the virB operon is under transcriptional regulation of the virB3 promoter.

The DNA fragment comprising the 3' end of the virB operon of pTiBo542 under control of a virB1 promoter and the virG gene of pTiBo542 was subsequently introduced in a T-DNA vector by three way ligation between the about 1.6 kb XbaI-BglII fragment of pVE194, the about 1.3 kb BglII-SphI fragment of pVE194 and the about 7.2 kb XbaI-SphI fragment from pGSV8, comprising the T-DNA. The resulting plasmid was named pTVE197.

The selectable marker gene of pTCO114 was introduced in pTVE197 by ligation of the following three fragments:
  i) the about 5.3 kb BanII-BstEII fragment of pTVE197, comprising the 3' end of the virB and the virG gene;
  ii) the about 3.7 kb BanII-EcoRI fragment of pTVE197, comprising the right T-DNA border;
  iii) the about 4 kb EcoRI-BstEII fragment of pTCO114, comprising the chimeric selectable bar gene and the left T-DNA border;
  resulting in T-DNA vector pVE200.

1.3 Agrobacterium tumefaciens Strains

T-DNA vectors pGSV71, pTCO114, pTCO121, and pVE200 were introduced in Agrobacterium strains LBA4404 comprising the helper Ti-plasmid pAL4404 or EHA101, comprising the helper plasmid pEHA101, using the triparental mating protocol (Ditta et al., 1980), selecting for resistance to streptomycin (300 µg/ml) and spectinomycin (100 µg/ml). The following strains were used throughout the Examples.

Strain A3593: LBA4404 comprising pGSV71
Strain A3532: LBA4404 comprising pTCO0121
Strain A3638: LBA4404 comprising pVE200
Strain A3460: EHA101 comprising pTCO114
Strain A3533: EHA101 comprising pTCO121
Strain A3637: EHA101 comprising pVE200

EXAMPLES

Example 1

Agrobacterium-mediated Transformation of Acetosyringone Pre-treated Type I Callus from Corn Type I callus fragments were obtained essentially as described in WO 92/09696. Immature embryos from corn line (Pa91xH99)xH99 (PHH-line) were excised from the kernel 9–12 days after pollination, surface sterilized and plated on Mahi1VII medium for the induction of type I callus. Type I callus was subcultured on the same medium with one month intervals for about two to six months. Next, type I callus was finely cut in fragments with an average length of about 1.5 mm, and the resulting fragments were incubated for 5 days on LSIDhy1.5VII substrate supplemented with 100–200 µM acetosyringone. The pre-induced callus pieces were collected and without further wounding, immersed in a suspension of the appropriate Agrobacterium strain for about 3 to about 20 minutes. The bacterial suspension was obtained in the following way: bacteria were grown for 3 to 6 days on MAG medium [minimal A medium (Jeffrey Miller, 1972) supplemented with 2 g/L glucose] or AB medium (Chilton et al., 1974). The bacteria were harvested, and resuspended in liquid LSI substrate supplemented with 100–200 µM acetosyringone, at a concentration of about $5 \times 10^9$ cells/ml.

After immersion in the bacterial suspension, the callus fragments were co-cultivated on LSIIDhy1.5XI medium, supplemented with 100–200 µM acetosyringone, at about 25° C. for 3 to 6 days (3 days for LBA-type strain, 6 days for EHA-type strain).

After co-cultivation, the tissue was transferred to Ahx1.5VIIp500ino1000ppT10 and cultured for 3 to 4 weeks. Proliferating, phosphinotricin (PPT)-resistant calli were excised and subcultured at least twice, with 3 week subculture intervals on Mh1VIIp500ppT5. Embryogenic PPT-resistant calli were plated on regeneration medium (A37VIIp500 ppT2.), and the embryogenic tissue was subcultured twice, with 10 to 14 day intervals, on the same medium. Small plants were transferred to glass containers containing A6%VIIp500ppT2 substrate for further growth, and developing shoots were then transferred to half-strength MS medium supplemented with 1.5% sucrose to allow further shoot elongation as well as rooting. Plants were tested for phosphinothricin acetyl transferase (PAT) activity, and PAT-positive plants were transferred to the greenhouse. PAT-positive plants were tested for the presence of the transgene by Southern hybridization.

TABLE I

Summary of the mean transformation frequencies of Agrobacterium-mediated transformation of type I calli from the PHH corn line, with and without acetosyringone pretreatment.

| Agrobacterium strain | Approximate mean transformation frequency without pretreatment (%) | Approximate mean transformation frequency with pretreatment (%) |
|---|---|---|
| A3460 | <0.1 | 0.3 |
| A3533 | <0.1 | 0.8 |
| A3638 | <0.1 | 0.9 |
| A3637 | <0.1 | 0.8 |

In control experiments, wherein the Type I callus fragments were not pre-treated by incubation on acetosyringone containing media, co-cultivation with the Agrobacterium -strains described in the experimental section, the average transformation frequency never exceeded 0.1% (see Table I) although PAT-positive plants were obtained in each case.

The pretreatment with acetosyringone allowed an increase of at least three times in transformation efficiency of type I callus by co-cultivation with Agrobacterium strains. Co-cultivation of about 1700 callus fragments pre-treated with acetosyringone, with strain A3460, resulted in 5 PAT-positive lines (average transformation frequency of about 0.3%; see Table I).

Co-cultivation of about 4000 pre-treated callus fragments (for each series of experiments) with Agrobacterium strains A3638, A3533 and A3637 resulted in respectively 37, 30 and 33 PAT-positive plant lines (average transformation frequencies of about 1%). In these experiments, transformation efficiency was thus improved by at least about 7 to 10 times.

Enhancement of transformation frequency was also obtained for co-cultivation of type I calli obtained from corn plant lines (Pa91xH99)xPa91 (PHP) and Pa91 by pretreatment with acetosyringone.

Example 2

The presence of an Additional, Chimeric virB11 Gene Improves Agrobacterium-mediated Transformation Frequency.

Type I callus fragments were obtained as described in Example I and incubated for 5 days on LSIDhy1.5VII substrate supplemented with 100 $\mu$M of acetosyringone, followed by co-cultivation with Agrobacterium strain A3532 and A3638. For strain A3532 only I PAT-positive plant was obtained, even with acetosyringone pretreatment (transformation frequency<0.1%). However, the presence of the functional virB promoter preceding the virB11 open reading frame on the T-DNA vector, improved the transformation efficiency (see Table I) at least almost ten times.

Example 3

Agrobacterium-mediated Transformation of Type I Callus from Corn, Pretreated with Different Plant Phenolic Compounds Type I callus fragments were obtained as described in Example 1 and incubated for 5 days on LSIDhy1.5VII substrate supplemented with 100 $\mu$M of the plant phenolic compounds of Table II. Approximately 200 pre-induced callus fragments were co-cultivated with Agrobacterium strain A3637 (or A3638). The number of PAT-positive lines and transformation frequencies obtained are summarized in Table II.

TABLE II

Effect of different plant phenolic compounds on Agrobacterium-mediated transformation frequency.

| Plant phenolic compound | Number of PAT-positive lines | Transformation frequency (%) |
| --- | --- | --- |
| gallic acid | 3 | 1.5 |
| vanillin | 4 | 2 |
| catechol | 1 | 0.5 |
| 3,4-dihydroxybenzoic acid | 2 | 1 |
| p-hydroxybenzoic acid | 2 | 1 |
| acetosyringone | 2 | 1 |
| 2,4-dihydroxybenzoic acid | 1 | 0.5 |

Example 4

Pretreatment of Type I Callus from Corn with Acetosyringone, Improves Transformation Frequency by Electroporation Finely chopped pieces of calli, derived from type I callus and pre-incubated for 5 days on 100 $\mu$M acetosyringone-containing medium, as described in Example 1, were subjected without further wounding to electroporation as described in WO92/09696. Briefly, about 50 callus pieces were resuspended in 100 $\mu$l EPM-KCl buffer and preplasmolyzed for 3 hr at room temperature. Next the callus pieces were washed in EPM+KCl buffer and transferred to an electrocuvette in EPM+KCl buffer. Plasmid DNA (10 $\mu$g of pDE110) was added, and the DNA was incubated with the callus fragments for about 1 hr at room temperature. Electroporation was carried out using standard conditions (1 pulse with initial field strength 375 V/cm from a 900 $\mu$F capacitor). The calli were never kept on ice. Phosphinotricin-resistant calli were selected and plants regenerated as described (WO92/09696). Phosphinotricin acetyl transferase activity was detected as described (WO92/09696).

Whereas 13 PAT-positive plants were obtained by control electroporation of about 5640 callus pieces which were not pre-treated with acetosyringone (about 0.23%), 4 PAT-positive plants were obtained by electroporation of about 530 callus pieces pre-treated with acetosyringone (about 0.75%). Transformation frequencies were thus about three times higher when the finely-cut type I callus pieces were pre-treated by incubation for 5 days on 100 $\mu$M acetosyringone-containing media.

Example 5

Combination of Plant Phenolics Further Enhances the Transformation Frequency

Type I callus fragments were obtained as described in Example 1 and incubated for 5 days on LSIDhy1.5VII substrate supplemented with either 200 $\mu$M of acetosyringone or a combination of 100 $\mu$M acetosyringone and 100 $\mu$M p-hydroxybenzoic acid. About 250 callus pieces were co-cultivated with Agrobacterium strain A3533. Whereas 2 shoot-regenerating lines (comprising 1 PAT-positive line) were obtained on PPT containing media after pre-induction on acetosyringone (frequency about 1%), 7 shoot regenerating lines (comprising 5 PAT-positive lines) were obtained on PPT containing media after pre-induction on acetosyringone plus p-hydroxybenzoic acid (frequency about 3%).

Example 6

Analysis of the Transgenic Corn Plants, Obtained by Agrobacterium Mediated-transformation, of Examples 1 to 5

Transgenic corn plants of the previous examples were analyzed by Southern analysis.

In first instance, it was verified whether all transgenic plants which were regenerated from one single transgenic callus line were identical or whether they could have originated from independent transformation events. All regenerated plants obtained from 24 independent transgenic callus lines were analyzed by Southern and 37 different types of T-DNA integration were identified. In other words, the 24 plant lines (as defined in the description) represented at least 37 independent transformation events. Transformation frequencies expressed as the number of transgenic plant lines obtained per 100 callus pieces transformed are thus underestimates of the actual transformation frequencies.

Next, the copy number of the transgenes in different corn lines were analyzed by Southern hybridization. The majority of the analyzed transformed lines (T0) showed a rather simple T-DNA integration pattern (less than 4 copies).

Approximately ⅓ of the analyzed transgenic lines (56/148) had a single copy T-DNA integration. Only a limited number of lines (<10%) had a more complex T-DNA integration pattern (>4 copies).

Transgenic corn plants of the previous examples were also analyzed for segregation pattern of the transgenes in the progeny. A Basta herbicide spray was used to monitor the segregation of PAT activity in 113 plants regenerated from 57 independent transgenic callus lines. In the progeny of 74 plants regenerated from 32 independent transgenic callus lines, a 1:1 segregation of the PAT activity was observed, indicating that in the T0 plants the herbicide resistant transgene was present in one copy or in several, closely linked copies. In the progeny of 31 plants regenerated from 18 independent transgenic callus lines all plants were tolerant to the Basta herbicide spray or significantly more plants were tolerant than sensitive, indicating that in the T0 plants 2 or more unlinked copies of the transgene were present. Finally, in the progeny of 14 plants regenerated from 7 independent transgenic callus lines no tolerant plants were observed or significantly more plants were sensitive than tolerant. These latter plants were not further analyzed.

Southern analysis of 2 plants of the T1 progeny resistant to Basta herbicide for each of 53 independently transformed corn plants (T0) revealed that in approximately 70% of the analyzed cases (35/53) both progeny plants had an identical T-DNA integration pattern as the T0 parent plant line. Segregation was observed in approximately 18% of the cases (10/53).

REFERENCES

Ashby et al. (1988) *J. Bacteriol.* 170: 4181–4187
Ausubel et al. (1994) *Current Protocols in Molecular Biology, Current Protocols*, USA.
Bolton et al. (1986) *Science* 232: 983–985;
Bytebier et al. (1987) *Proc. Natl. Acad. Sci. USA* 84: 5345–5349
Chan et al. (1993) *Plant Mol. Biol.* 22: 491–506
Chen and Winans (1991) *J. Bacteriol* 173: 1139–1144
Chilton et al. (1974) *Proc. Natl. Acad. Sci. USA* 71: 3672–3676
Chu et al. (1975) *Sci. Sin. Peking*, 18, 659–668
Christou (1 994) *Agro-Food Industry Hi-Tech* 17–27
Cornelissen and Vandewiele (1989) *Nucl. Acids Res.* 17: 833-.
R. D. D. Croy (1993) Plant Molecular Biology Labfax BIOS Scientific Publications Ltd (UK) and Blackwell Scientific Publications, UK.
Das et al. (1986). *Nucl. Acids Res.* 14: 1355–1364
Deblaere et al. (1987) *Meth. Enzymol* 153: 277–293
De Block et al.(1987) *EMBO J* 6: 2513–2518).
Ditta et al. (1980) *Proc. Natl. Acad. Sci. USA* 77: 7347–7351
Guivarc'h et al. (1993) *Protoplasma* 174: 10–18
Hansen et al. (1994) *Proc. Natl. Acad. Sci. USA* 91:7603–7607
Hernalsteens et al. (1984) EMBO J.
Hooykaas-Van Slogteren et al. (1984) *Nature* 311:763–764
Jacq et al. (1993) *Plant Cell Reports* 12: 621–624
James et al. (1993) *Plant Cell Reports* 12: 559–563)
Jarchow et al. (1991), *Proc. Natl. Acad. Sci. USA* 88:10426–10430
Klapwijk et al. (1980) *J. Bacteriol.,* 141, 128–136
Liu et al. (1992) *Plant Mol Biol.* 20: 1071–1087
Mariani et al. (1990) *Nature* 347: 737–741
Mariani et al. (1992) *Nature* 357: 384–387
Miller (1972) "Experiments in Molecular Genetics" Cold Spring Harbor Lab., Cold Spring Harbor, New York
Mooney et al. (1991) *Plant Cell, Tissue, Organ Culture* 25: 209–218
Murashige and Skoog (1968) *Physiol Plant* 15, 473–497
Potrykus (1991) *Annu. Rev. Plant Physiol Plant Mol. Biol.* 42, 205–225
Raineri et al. (1990) *Bio/technology* 8: 33–38
Sambrook et al. (1989) *Molecular Cloning: A Laboratory Manual*, Second Edition, Cold Spring Harbor Laboratory Press, NY
Scheeren-Groot et al. (1994) *J. Bacteriol* 176: 641 8–6426
Stachel et al. (1985) *Nature* 318: 624–629
Stachel and Nester (1986) *EMBO J.* 5: 1445–1454
Van Laerebeke et al. (1974) *Nature* 252,169–170
Van Wordragen and Dons (1992) *Plant Mol. Biol. Rep.* 10: 12–36
Vasil (1994) *Plant Mol. Biol.* 25: 925–937
Vernade et al. (1988) *J. Bacteriol.* 170: 5822–5829
Watson et al. (1975) *J. Bacteriol* 123, 255–264

What is claimed is:

1. A process for integrating a DNA fragment into the genome of a cell of a monocotyledonous plant, the process comprising the step of
   a) cocultivating a culture of untransformed monocotyledonous plant cells with an Agrobacterium strain comprising said
   DNA fragment under conditions in which the DNA fragment is taken up by the untransformed cells and is stably integrated in the genome of the untransformed cells to generate transformed cells
   wherein said Agrobacterium strain comprises an extra copy of a chimeric gene comprising a virB11 coding region operably linked to a promoter capable of expression in Agrobacterium.

2. The process of claim 1, further comprising the step of regenerating a transgenic monocotyledonous plant from said transformed cells.

3. The process of claim 1, wherein said virB 11 coding region is derived from pTiBo542.

4. The process of claim 1, wherein said promoter capable of expression in Agrobacterium is a virB promoter.

5. The process of claim 1, wherein said virB11 coding region is operably linked to said promoter capable of expression in Agrobacterium with the proviso that no other coding regions of the virB operon are located between said virB11 coding region and said promoter capable of expression in Agrobacterium.

6. The process of claim 1, wherein said Agrobacterium strain has a bacterial chromosomal background of LBA4011 and further comprises helper plasmid pAL4404.

7. The process of claim 1, wherein said Agrobacterium strain has a bacterial chromosomal background of C58C1 and further comprises helper plasmid pEHA101.

8. The process of claim 1, wherein said monocotyledonous plant is corn, rice, wheat or barley.

9. The process of claim 1, wherein said monocotyledonous plant is corn.

10. The process of claim 9, wherein said culture of untransformed monocotyledonous plant cells is a type I callus.

* * * * *